United States Patent
Garino

(10) Patent No.: US 11,963,878 B2
(45) Date of Patent: Apr. 23, 2024

(54) CRUCIATE REPLACING ARTIFICIAL KNEE

(71) Applicant: Jonathan P. Garino, Villanova, PA (US)

(72) Inventor: Jonathan P. Garino, Villanova, PA (US)

(*) Notice: Subject to any disclaimer, the term of this patent is extended or adjusted under 35 U.S.C. 154(b) by 535 days.

(21) Appl. No.: 17/082,568

(22) Filed: Oct. 28, 2020

(65) Prior Publication Data

US 2021/0038399 A1 Feb. 11, 2021

Related U.S. Application Data

(62) Division of application No. 16/292,467, filed on Mar. 5, 2019, now Pat. No. 11,129,720.

(51) Int. Cl.
*A61F 2/38* (2006.01)
*A61F 2/08* (2006.01)
*A61F 2/30* (2006.01)

(52) U.S. Cl.
CPC .......... *A61F 2/3836* (2013.01); *A61F 2/3859* (2013.01); *A61F 2/3886* (2013.01); *A61F 2/389* (2013.01); *A61F 2/08* (2013.01); *A61F 2002/30362* (2013.01); *A61F 2002/30369* (2013.01); *A61F 2002/30462* (2013.01); *A61F 2002/30523* (2013.01); *A61F 2002/30621* (2013.01); *A61F 2220/0025* (2013.01)

(58) Field of Classification Search
CPC .......... A61F 2/38; A61F 2/386; A61F 2/3845; A61F 2/3859; A61F 2/3886; A61F 2/389
See application file for complete search history.

(56) References Cited

U.S. PATENT DOCUMENTS

| | | | |
|---|---|---|---|
| 3,969,773 | A | 7/1976 | Menschik |
| 5,011,496 | A | 4/1991 | Forte et al. |
| 5,871,543 | A | 2/1999 | Hofmann |
| 5,935,133 | A | 8/1999 | Wagner et al. |
| 6,325,828 | B1 | 12/2001 | Dennis et al. |
| 6,517,504 | B1 | 2/2003 | Postelmans |
| 6,629,999 | B1 | 10/2003 | Serafin |

(Continued)

FOREIGN PATENT DOCUMENTS

| | | |
|---|---|---|
| DE | 69305434 T2 | 11/1997 |
| EP | 0103697 A1 | 3/1984 |

(Continued)

OTHER PUBLICATIONS

D'Alessio et al., "On the Application of RRSS Motion Generation and RRSS Axode Generation for the Design of a Cncept Prosthetic Knee", Aug. 3, 2016, Mechanics Based Design of Structures and Machines: An International Journal, Taylor and Francis, pp. 1-10 (Year: 2016).*

(Continued)

*Primary Examiner* — Marcia L Watkins
(74) *Attorney, Agent, or Firm* — Buchanan Ingersoll & Rooney PC

(57) ABSTRACT

A knee joint prosthesis is capable of moving between an extended position and a flexion position. The knee joint prosthesis includes a femoral component that is configured to be mounted to a femur, and a tibial component that is configured to be mounted to a tibia. The femoral component and the tibial component are at least partially connected together by a geared arrangement.

6 Claims, 11 Drawing Sheets

(56) References Cited

U.S. PATENT DOCUMENTS

| | | |
|---|---|---|
| 6,660,039 B1 | 12/2003 | Evans et al. |
| 8,480,752 B2 | 7/2013 | Dun |
| 8,858,207 B2 | 10/2014 | Evans |
| 9,387,084 B2 | 7/2016 | Masini et al. |
| 9,861,484 B2 | 1/2018 | Sanford et al. |
| 9,861,489 B2 | 1/2018 | Siebel |
| 10,292,826 B2 | 5/2019 | Wyss et al. |
| 10,682,236 B2 | 6/2020 | Boettiger |
| 2003/0199985 A1 | 10/2003 | Masini |
| 2005/0187635 A1 | 8/2005 | Metzger |
| 2005/0209702 A1 | 9/2005 | Todd et al. |
| 2010/0016979 A1 | 1/2010 | Wyss et al. |
| 2012/0095563 A1 | 4/2012 | Sanford et al. |
| 2012/0221113 A1 | 8/2012 | Katrana et al. |
| 2015/0182344 A1 | 7/2015 | McKinnon et al. |
| 2015/0190236 A1* | 7/2015 | McMinn .............. A61F 2/3886 623/20.27 |
| 2017/0252173 A1 | 9/2017 | Garino |
| 2017/0333193 A1 | 11/2017 | Miura et al. |
| 2018/0325681 A1* | 11/2018 | Lee ........................ A61F 2/384 |
| 2019/0029847 A1 | 1/2019 | Nguyen et al. |
| 2020/0281732 A1 | 9/2020 | Garino |
| 2021/0007855 A1 | 1/2021 | Collazo et al. |
| 2022/0183856 A1* | 6/2022 | Mahfouz .............. A61B 17/157 |

FOREIGN PATENT DOCUMENTS

| | | | |
|---|---|---|---|
| JP | 2013501555 A | 1/2013 | |
| WO | 2011150238 A1 | 12/2011 | |
| WO | 2013009966 A2 | 1/2013 | |
| WO | 2013063314 A1 | 5/2013 | |
| WO | 2018085329 A1 | 5/2018 | |

OTHER PUBLICATIONS

Extended European Search Report for European Application No. 19214530.8, dated Nov. 19, 2020, 12 pages.
Extended European Search Report for European Application No. 21208113.7, dated Apr. 20, 2022, 9 pages.
Non Final Office Action for U.S. Appl. No. 17/167,194, dated May 12, 2022, 16 pages.
Non Final Office Action for U.S. Appl. No. 16/950,074, dated Mar. 10, 2023, 27 pages.
Extended European Search Report for European Application No. 21200764.5, dated Dec. 23, 2021, 7 pages.
Extended European Search Report for European Application No. 21200744.7, dated Jan. 4, 2022, 8 pages.
Partial European Search Report for European Application No. 19 214 530.8, dated Jul. 21, 2020, 12 pages.
Entire patent prosecution history of U.S. Appl. No. 16/292,467, filed Mar. 5, 2019, entitled, "Cruciate Replacing Artificial Knee."
Non Final Office Action for U.S. Appl. No. 16/950,304, dated Apr. 3, 2023, 26 pages.
Japanese Notice of Reasons for Rejection for Japanese Application No. 2019-206156, dated Aug. 29, 2023 with translation, 8 pages.

* cited by examiner

CRUCIATE REPLACING ARTIFICIAL KNEE

CROSS-REFERENCE TO RELATED APPLICATIONS

This invention is a divisional patent application of U.S. patent application Ser. No. 16/292,467, filed Mar. 5, 2019, which is incorporated by reference herein in its entirety.

FIELD OF THE INVENTION

This invention relates generally to artificial knee prostheses used for Total Knee Replacement (TKR), and more particularly, to a knee joint prosthesis having an artificial anterior cruciate ligament (ACL) and/or posterior cruciate ligament (PCL).

BACKGROUND OF THE INVENTION

As is described in U.S. Patent App. Pub. No. 2017/0252173 to Garino, which is incorporated by reference herein in its entirety and for all purposes, prosthetic knees generally include three main components, a femoral component (FIGS. 1A and 1B), which is attached to the distal end of the femur, a tibial component (FIGS. 2A and 2B), which is implanted onto the proximal end of the tibia, and an articular insert (FIGS. 3A and 3B), which is mounted onto the tibial component and provides a frictional surface for the femoral component. The components are designed to simulate a joint and the associated mechanics of a human knee throughout the knee's range of motion. The components are generally provided in a variety of shapes with varying dimensions (identified as dimensions A-H and J-T in FIGS. 1A to 3B), so that a physician is able to select the optimal combination of components depending on the specific anatomy of the patient. The size and shape of the knee is dependent on various factors including age, gender, and size of the patient. Therefore, a fairly large inventory of components are generally made available, so that the prosthetic knee may be tailored for the patient.

During the course of a routine knee construction with a TKR, the ACL is removed in a vast majority of all cases and depending on the selected TKR design, the patient's PCL is either retained or substituted with some mechanism to replace the lost function of the PCL. Even when the PCL is retained, often a portion of the PCL must be cut or partially cut during surgery to aid in the balancing of the knee replacement. When the PCL is completely removed, the PCL is substituted by a post and cam mechanism.

A TKR generally comprises a femoral component 10, a tibial component 16, and an articular insert 22 that resides on a top mounting portion 20 of a tibial component 16 for interfacing with the femoral component 10. Referring to FIGS. 1A, 1B, 3A, and 3B, an illustration of a typical design of a post and cam mechanism is provided. An articular insert 22 includes an extension 24 that protrudes into an opening 12 of the femoral component 10. A box 11 having upwardly projecting walls is formed on the interior side of the femoral component 10 and includes an interior region that intersects the opening 12. The extension 24 includes a posterior surface 25 that is intended to be in frictional contact with the posterior surface 14 of the opening 12 when the joint is flexed. The resistance generated when the extension 24 bears against the posterior surface 14 of the opening 12 in the femoral component 10 is intended to simulate the resistance that would have been generated by a healthy posterior cruciate ligament (PCL).

Cam and post mechanisms have been manufactured that partially replace the function of an ACL by creating a cam surface between the anterior surface of the extension 24 and the anterior surface of the opening 12; however, this solution provides only a partial substitution of an ACL because the anterior side of the extension 24 is at best able to contact the anterior side of the opening only between 0 to 20 degrees of flexion.

Another solution is to connect the femoral component and tibial component with a cable-like material, such as the material disclosed in U.S. Pat. No. 5,935,133, the contents of which are incorporated herein by reference. But this artificial material is typically only used to replace the PCL and not the ACL.

The lack of an anatomically correct replacement may result in a TKR having reduced functionality as compared to the original knee. This may create difficulties during physical therapy following surgery, as well as limit the patient's ability or desire to participate in physical activity following therapy. Virtually all modern total knee replacements sacrifice the ACL or inadequately substitute it with a crude cam and post mechanism, thus leaving the reconstructed knee with kinematics similar to that of an ACL-deficient knee. Normal knee kinematics therefore remain elusive. In addition, the lack of proper interplay between an ACL and PCL (which together drive normal knee kinematics) leaves the TKR reconstruction short of producing a relatively normal knee for the patient.

Given the complexity of the mechanics of a knee joint and the difficulty for patients to adjust to an artificial knee after surgery, an anatomically correct knee replacement system is needed that more accurately simulates the resilience and support formerly provided by the removed ligaments. In order to provide a more anatomically correct TKR, prosthesis embodiments that replicate the function provided by both the ACL and PCL are desirable.

Referring now to FIG. 4, a healthy human knee is illustrated with a loop 30, representing an exemplary artificial ACL/PCL ligament, drawn over the location of the original anatomical ACL and PCL. The section of the loop 30 constituting the artificial PCL is bounded by points 26A and 26B. The section of the loop 30 constituting the artificial ACL is bounded by points 28A and 28B.

Referring now to FIGS. 5, 6A, and 6B illustrating an embodiment disclosed in U.S. Patent App. Pub. No. 2017/0252173 to Garino, the connection points 26a, 26b, 28a, and 28b of the artificial material, provided as ligament 44, and the lengths spanning between the connection points, provided as an outline of the artificial ligament 44, are configured to simulate the dimensions and attachment points of the ACL and PCL in a human knee, as illustrated in FIG. 4. At least one length of artificial ligament may be provided to connect the articular insert 22 and femoral component 10 of a TKR.

While U.S. Patent App. Pub. No. 2017/0252173 to Garino provides solutions to these complexities, developments in this area are continually sought in the interest of improving the mechanics of a knee joint.

SUMMARY OF THE INVENTION

In one embodiment of the present invention, a knee joint prosthesis is capable of moving between an extended position and a flexion position. The knee joint prosthesis comprises a femoral component that is configured to be mounted to a femur, and a tibial component that is configured to be mounted to a tibia, the tibial component being configured to be engaged with the femoral component to form the knee joint prosthesis. A first post is fixedly connected to one of the femoral component and the tibial component, and a first cam recess is defined on the other of the femoral component and the tibial component that is configured to be engaged by the first post in either the extended position or the flexion position of the knee joint prosthesis. A second post is fixedly connected to one of the femoral component and the tibial component, and a second cam recess is defined on the other of the femoral component and the tibial component that is configured to be engaged by the second post in either the extended position or the flexion position of the knee joint prosthesis.

In another embodiment of the present invention, a knee joint prosthesis comprises a femoral component that is configured to be mounted to a femur, and a tibial component that is configured to be mounted to a tibia, the tibial component being configured to be engaged with the femoral component to form the knee joint prosthesis. A post is fixedly connected to one of the femoral component and the tibial component, and a cam recess is defined on the other of the femoral component and the tibial component and is configured to be engaged by the first post in either the extended position or the flexion position of the knee joint prosthesis. An artificial ligament is fixedly connected to the femoral component and the tibial component to simulate either an anterior cruciate ligament or a posterior cruciate ligament. The post and the ligament are oriented cross-wise as viewed in a sagittal plane, a frontal plane, or both the sagittal plane and the frontal plane.

In yet another embodiment of the present invention, a knee joint prosthesis comprises a femoral component configured to be mounted to a femur, and a tibial component configured to be mounted to a tibia. The tibial component is configured to engage the femoral component to form the knee joint prosthesis. The femoral component and the tibial component are at least partially connected together by a geared arrangement.

DETAILED DESCRIPTION

The present invention provides various embodiments of a knee joint prosthesis. In the figures, 'A' represents the anterior side or direction, 'P' represents the posterior side or direction, 'M' represents the medial side or direction, 'L' represents the lateral side or direction, 'F' represents a femoral component, and 'T' represents a tibial component (or an articular insert that forms part of a tibial component).

Figure 1A:
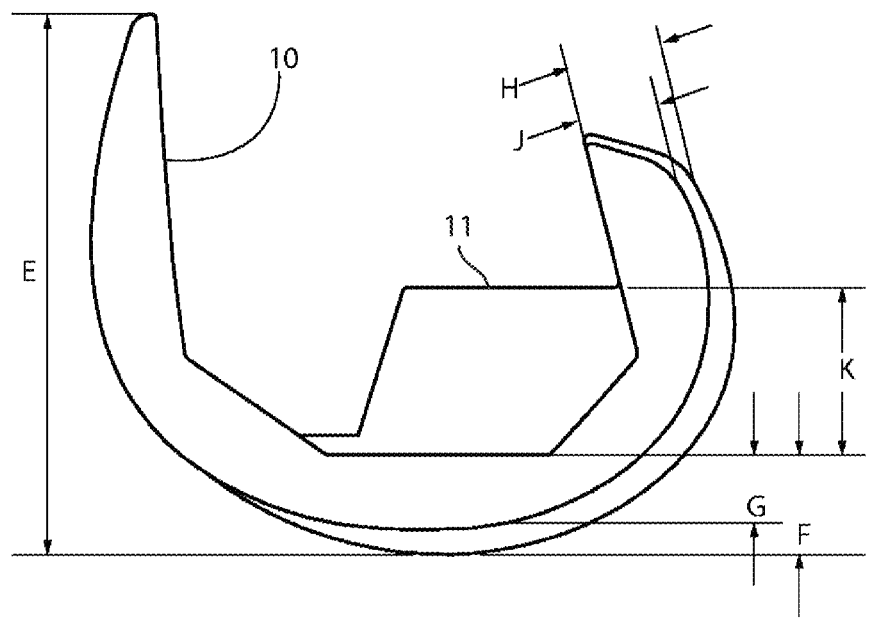
FIG. 1A is a side view of a femoral component for a knee joint prosthesis known by those of ordinary skill in the art.
Figure 1B:
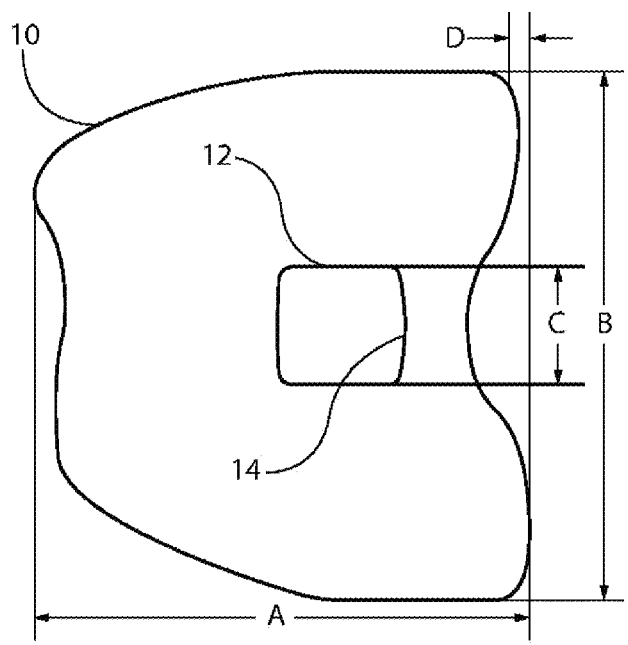
FIG. 1B is a bottom view of the femoral component of FIG. 1A.
Figure 2A:
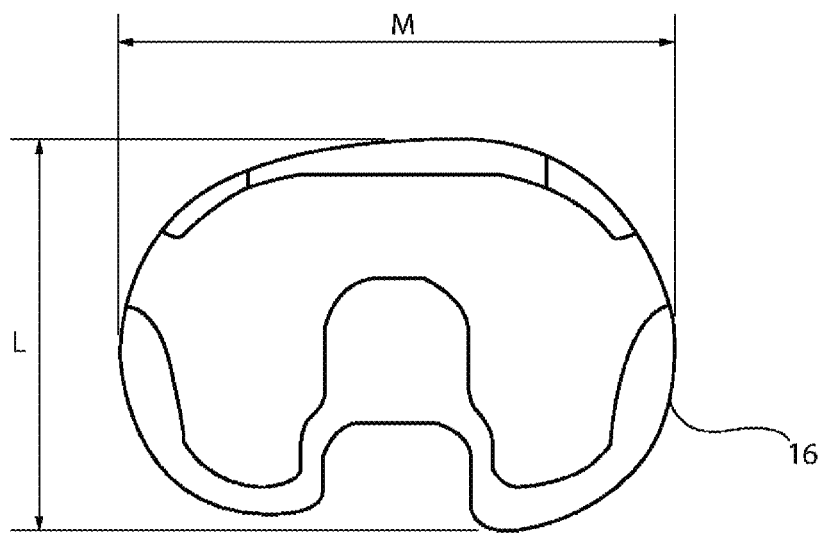
FIG. 2A is a top view of a tibial component for a knee joint prosthesis known by those of ordinary skill in the art.
Figure 2B:
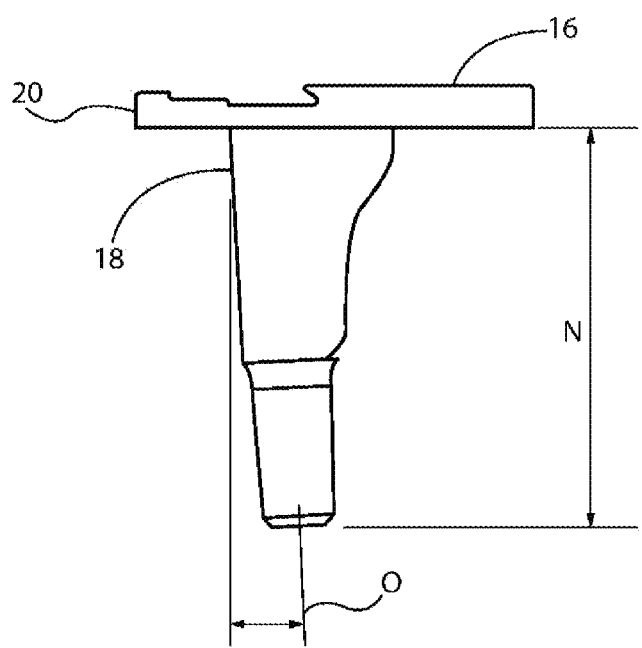
FIG. 2B is a side view of the tibial component of FIG. 2A.
Figure 3A:
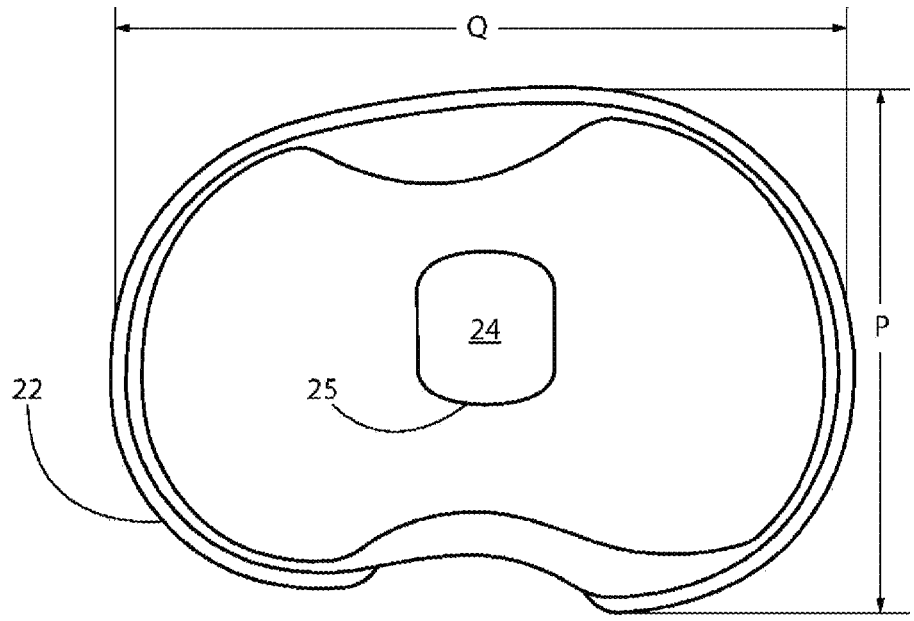
FIG. 3A is a top view of an articular insert for a knee joint prosthesis known by those of ordinary skill in the art.
Figure 3B:
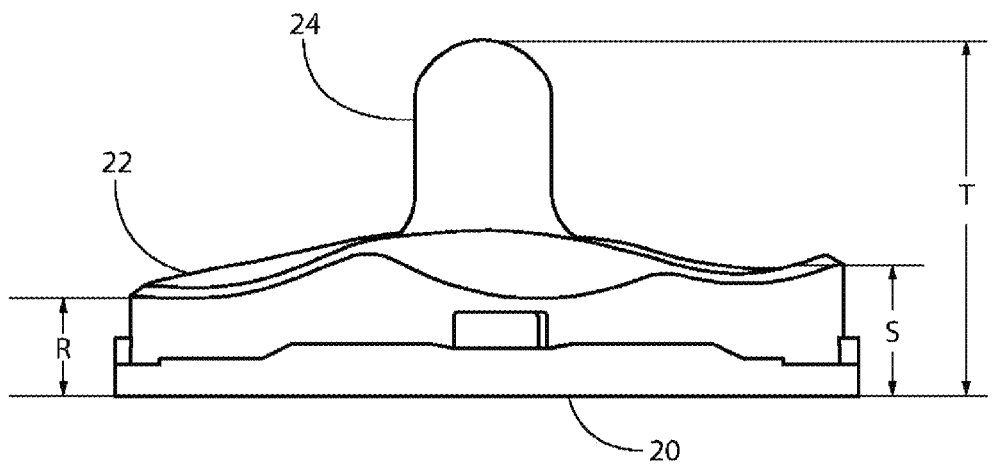
FIG. 3B is a front view of the articular insert of FIG. 3B mounted on the baseplate of a tibial component.
Figure 4:
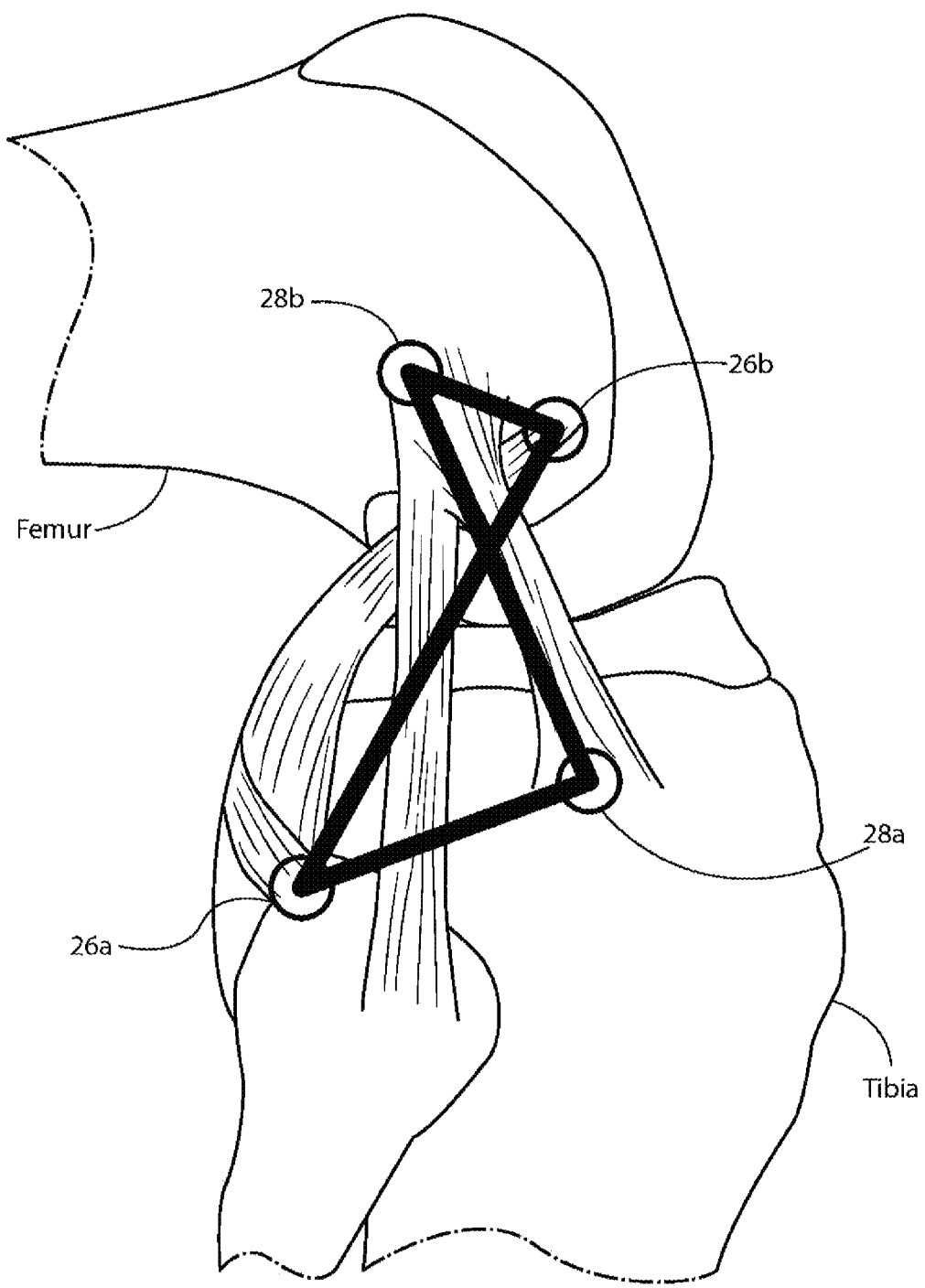
FIG. 4 is a side view of a knee joint illustrating the anatomical location of the ACL and PCL and the configuration of an artificial material intended to replace the ACL and PCL.
Figure 5:
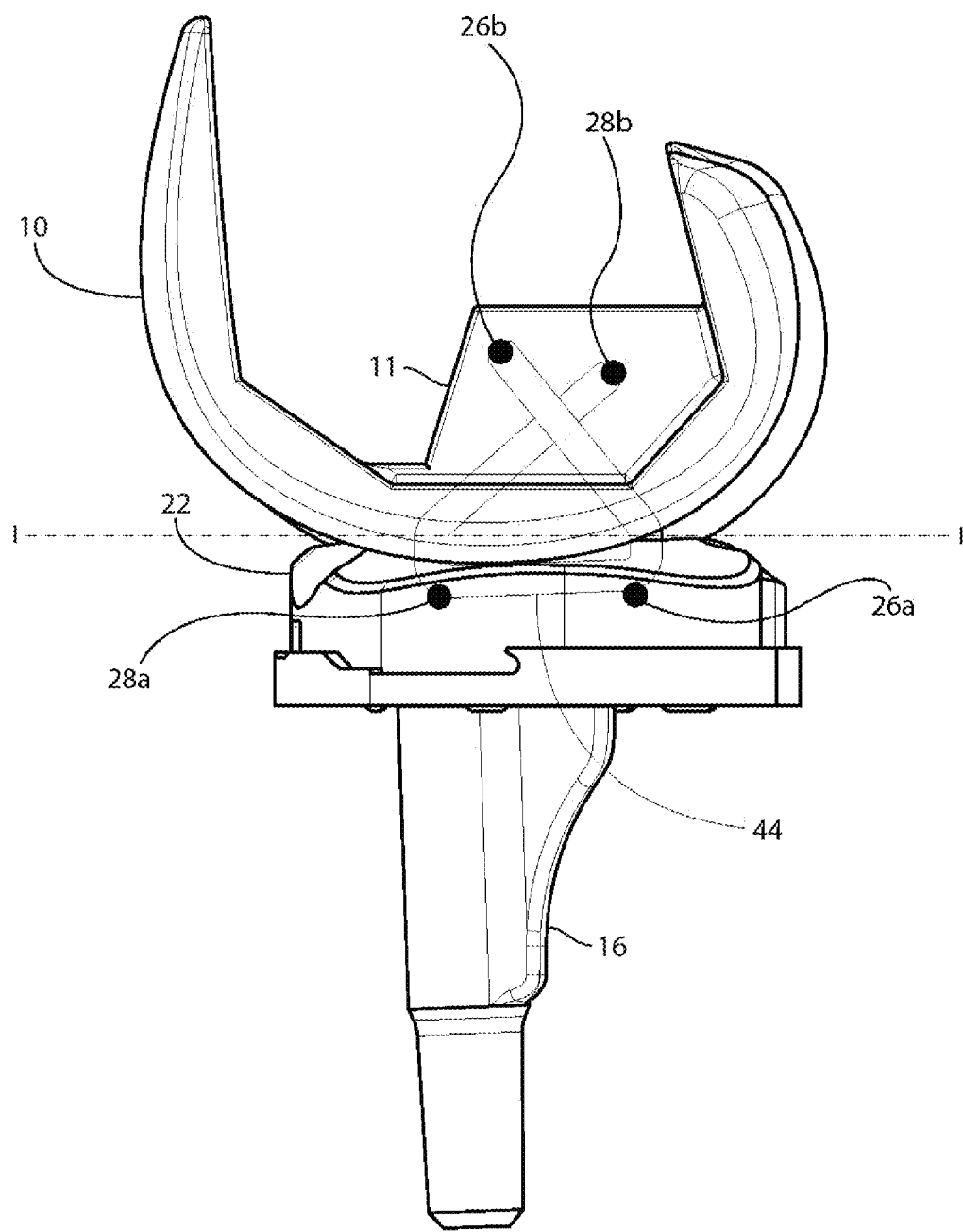
FIG. 5 is a side view of a femoral component, articular insert, and artificial ligament for a TKR according to the prior art.
Figure 6A:
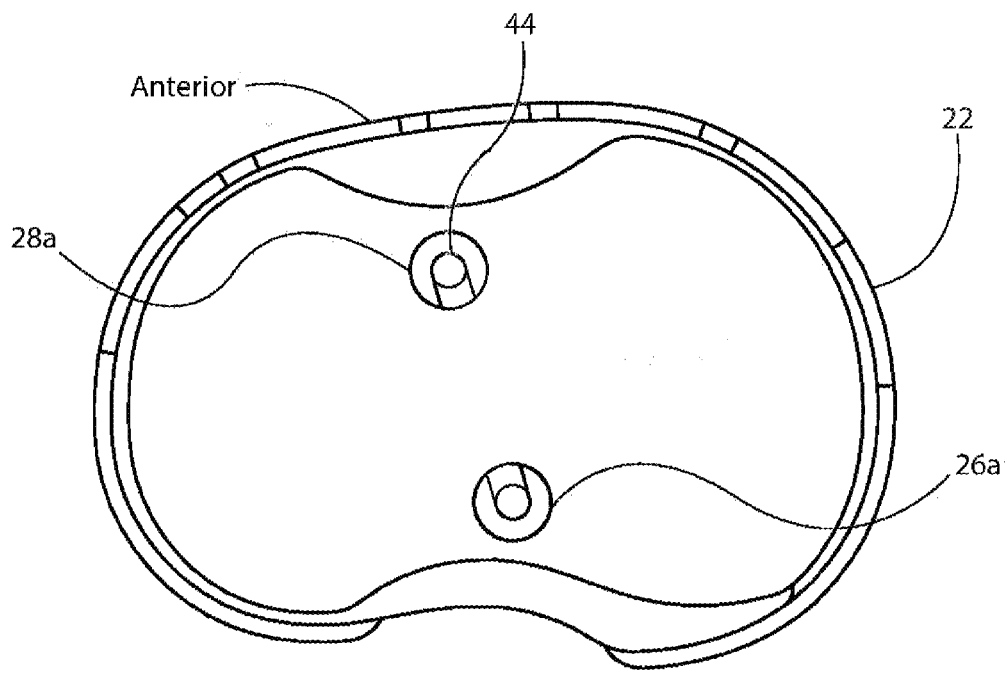
FIG. 6A is a top view of a cross-section along line I-I of FIG. 5.
Figure 6B:
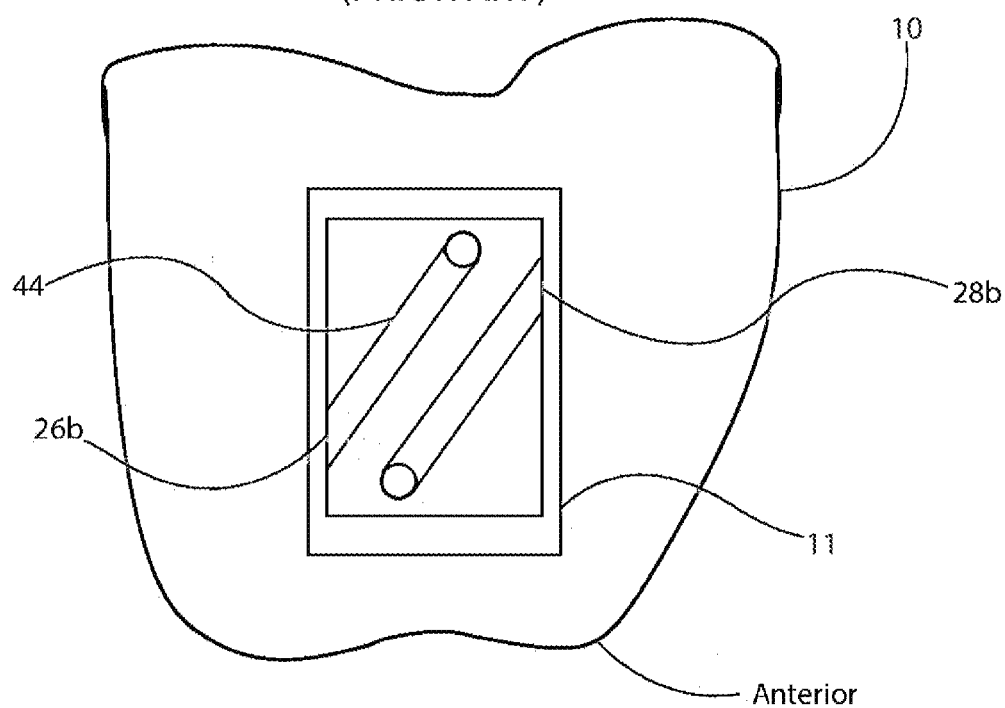
FIG. 6B is a bottom view of a cross-section along line I-I of FIG. 5.
Figure 7A:
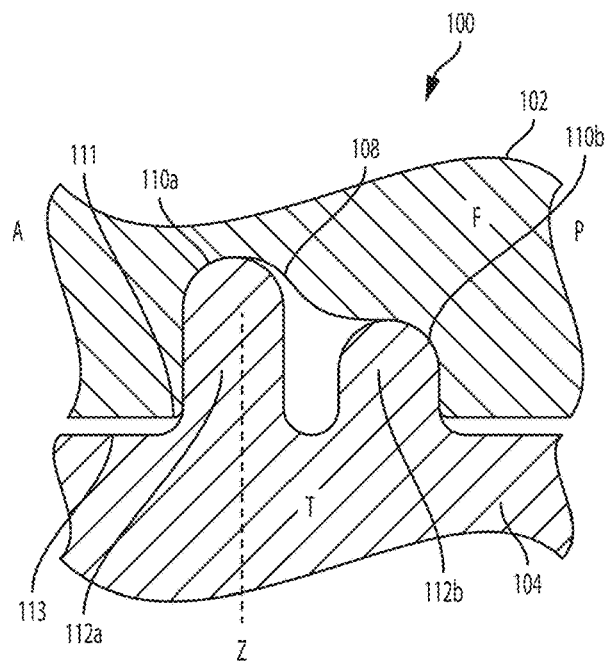
FIG. 7A is a cross-sectional side elevation view of a knee joint prosthesis, as viewed in a sagittal plane, according to an exemplary embodiment of the present invention, wherein the knee joint prosthesis is shown in an extended position.
Figure 7B:
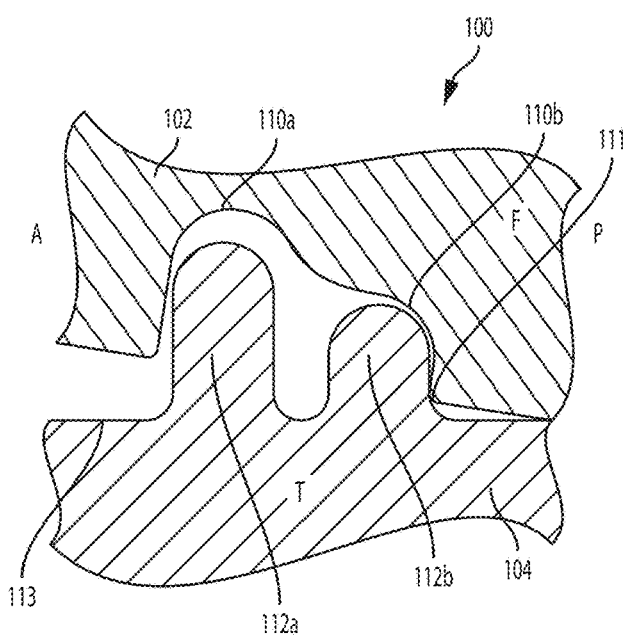
FIG. 7B is another view of the knee joint prosthesis of FIG. 7A, wherein the knee joint prosthesis is shown in a flexion position.

FIG. 7A is a cross-sectional side elevation view of a knee joint prosthesis 100, as viewed in a sagittal plane, according to an exemplary embodiment of the present invention, wherein the knee joint prosthesis 100 is shown in an extended position. FIG. 7B is another view of the knee joint prosthesis 100 of FIG. 7A, wherein the knee joint prosthesis 100 is shown in a flexion position. The knee joint prosthesis 100 is capable of rotating between the extended position of FIG. 7A and the flexion position of FIG. 7B.

The prosthesis 100 generally comprises a femoral component 102 and an articular insert 104 that is either mounted to or forms part of a tibial component.

The femoral component 102 shown in FIGS. 7A and 7B may represent a femoral component (like item 10) having condoyles, or a box (like box 11) that is mounted to the femoral component. A recess 108 is formed on the lower end of femoral component 102. The recess 108 is located between the condyles 106 along the medial-lateral direction. An edge 111 is formed at the semi-circular boundary of the recess 108 at the location where the recess 108 intersects the exterior surface of the femoral component 102. The recess 108 is positioned at the same approximate location as the opening 12 in the femoral component 10. Unlike the opening 12, however, the recess 108 is blind, and includes a smooth and rounded interior surface. Two cam surfaces 110a and 110b (referred to either individually or collectively as cam surface(s) 110) are formed at opposing ends of the interior surface of the recess 108. Each cam 110 is a smooth and rounded concave surface. The radii of the cams 110 may be the same or different. The cams 110 are configured to interact with rounded posts 112a and 112b extending from the top surface of the articular insert 104.

The articular insert 104 is similar to the articular insert 22, and the primary differences between those inserts will be described hereinafter. The articular insert 104 includes the two posts 112a and 112b (referred to either individually or collectively as post surface(s) 112) that extend from the bearing surface 113. Post 112a corresponds to the ACL, whereas the post 112b corresponds to the PCL. Each rounded post 112 terminates at a convexly rounded surface. The radius of each post 112 may be identical to or substantially the same as the radius of each cam 110. The extension height and radii of the posts 112 may be different (as shown) or the same to complement the geometry of the mating cams 110. According to this embodiment, the ACL post 112a has a greater height than the PCL post 112b. The posts 112 extend along their respective axes Z, which are orthogonal to bearing surface 113. Alternatively, the posts 112 may extend obliquely with respect to axis Z. The posts 112 of FIG. 7A, as well as all of the other posts described herein, may be integral with the articular insert 22 (or other component to which the post is connected), as shown, or connected to the articular insert 22 using mechanical threads, a bolt, friction, adhesive, cement, or any other means for mounting two components together that are known to those skilled in the art.

The articular insert 104 is capable of rotating relative to the femoral component 102 between the extended position of FIG. 7A and the flexion position of FIG. 7B. In the extended position of the knee joint prosthesis 100, the condyles may rest on the bearing surface 113 of the articular insert 104, and the posts 112 are positioned against their respective cams 110. As the femoral component 102 rotates relative to the articular insert 104, or vice versa, the post 112 rides along the surface of cam 110 until the edge 111 of the recess 108 bears on the base of the posterior post 112. The ACL post 112a may bear on its cam 110a. Although not shown, the collateral ligaments (MCL and LCL) adjacent to the knee joint prosthesis 100 prevent detachment of the femoral component 102 from the articular insert 104.

The arrangement of two posts 112 and two cams 110 more closely mimics the arrangement of the PCL and ACL, as compared to a traditional knee joint prosthesis having a single post and a single cam.

As noted above, the recess 108 may be formed in a separate insert, like box 11, that is capable of being attached to the femoral component 102. A series of inserts having different recess geometries may be provided as a kit, such that a medical professional can select the insert having a geometry that is best suited for the particular anatomy of a patient.

Figure 8:
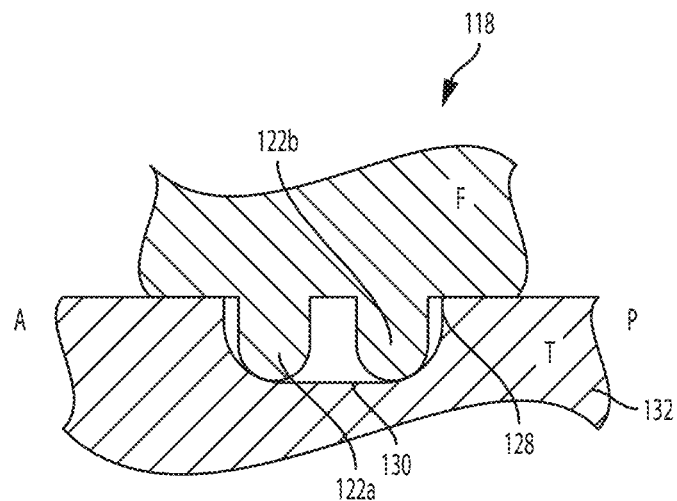
FIG. 8 depicts an alternative embodiment of a knee joint prosthesis, as viewed in a sagittal plane, in which the posts are disposed on the femoral portion and the cams are disposed on the tibial portion.

FIG. 8 depicts a knee joint prosthesis 118 in which the posts 122a and 122b are disposed on the femoral component 124 and the cams 128 are defined on a recess 130 that is disposed on the articular insert 132 of a tibial component. The knee joint prosthesis 118 is similar to the knee joint prosthesis 100 with the exception that the location of the posts and cams are switched. Operation of the knee joint prosthesis 118 is substantially similar to that of the knee joint prosthesis 100. Although not shown, like box 11, the posts 122a and 122b may be formed in a separate insert that is capable of being attached to the femoral component 124.

Figure 9:
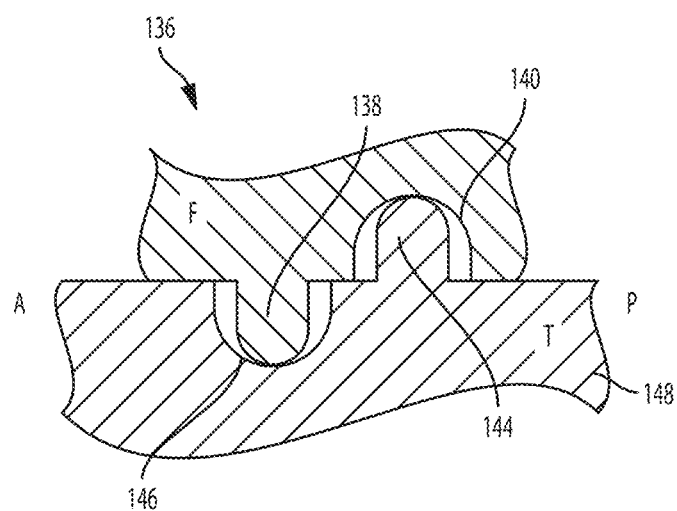
FIG. 9 depicts an alternative embodiment of the knee joint prosthesis, as viewed in a sagittal plane, in which one post and one cam is disposed on each of the femoral portion and the tibial portion.

FIG. 9 depicts a knee joint prosthesis 136. The knee joint prosthesis 136 is similar to the knee joint prosthesis 100 with the exception that one post 138 and one cam recess 140 are disposed on the femoral component 142, and one post 144 and one cam recess 146 are disposed on the articular insert 148 of a tibial component. In the extended position shown in FIG. 9, the post 138 of the femoral component 142 is mounted with the cam recess 146 of the tibial articular insert 148, and the post 144 of the tibial articular insert 148 is mounted with the cam recess 140 of the femoral component 142. Although the post 138 is disposed anterior of recess 140, it should be understood that the locations of the post 138 and the recess 140 may be switched (along with the locations of the recess 146 and the post 144). Operation of the knee joint prosthesis 136 is substantially similar to that of the knee joint prosthesis 100.

Figure 10A:
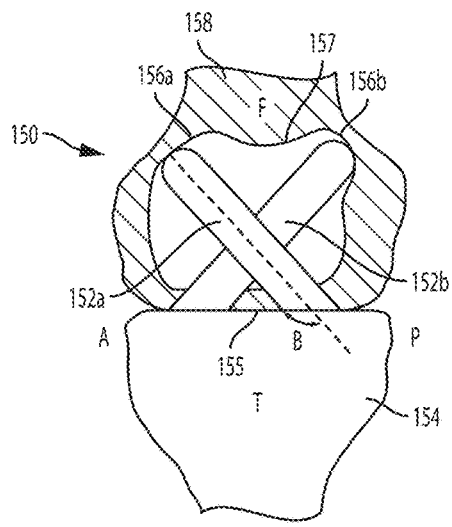
FIG. 10A depicts a partial cross-sectional view of an embodiment of a knee joint prosthesis, as viewed in a sagittal plane, in which posts, which mimic the ACL and PCL, are disposed on the tibial portion and engage with cams on the femoral portion.
Figure 10B:
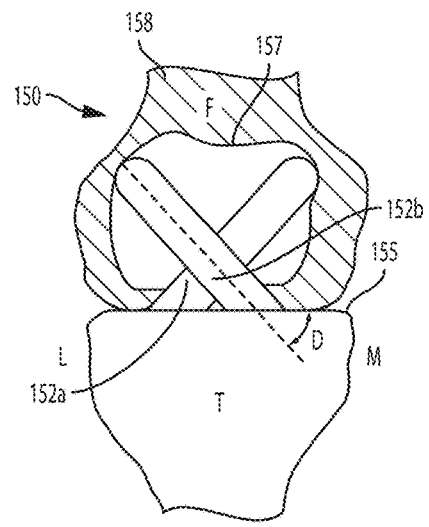
FIG. 10B depicts the knee joint prosthesis of FIG. 10A, as viewed in a frontal plane.

FIGS. 10A and 10B depicts an embodiment of a partial cross-sectional view of a knee joint prosthesis 150. The prosthesis 150 is similar to the prosthesis 100 and only the primary differences therebetween will be described. In the knee joint prosthesis 150, the posts 152a and 152b (referred to collectively as posts 152), which more closely mimic the PCL and ACL, respectively, are disposed on the articular insert 154 of a tibial portion (or the tibial portion itself) and engage with cams 156a and 156b (referred to collectively as cams 156), respectively, disposed on a recess 157 that is formed on the femoral component 158. The recess 157 extends upwardly from the bearing surface 155 of the prosthesis 150.

Specifically, the post 152a, which extends from the lateral and posterior sides of the articular insert 154 to the medial and anterior sides of the femoral component 158, more closely mimics the location and geometry of the PCL. The post 152b, which extends from the medial and anterior sides of the articular insert 154 to the lateral and posterior sides of the femoral component 158, more closely mimics the location and geometry of the ACL. The posts 152a and 152b are oriented cross-wise as viewed in the sagittal and frontal planes, however, the posts 152a and 152b may be oriented cross-wise as viewed in only one of those planes.

The angle 'B' of each post 152 with respect to the bearing surface 155, as viewed in a sagittal plane, may vary from that which is shown, and may be tailored to approximate the exact angle of an ACL or PCL. Similarly, the angle 'D' of each post 152 with respect to the bearing surface 155 of the articular insert 154, as viewed in a frontal plane, may vary from that which is shown, and may be tailored to approximate the exact angle of an ACL or PCL. It is noted that the angles B and D may be exaggerated in the figures. The length and diameter of each post 152 may vary from that which is shown, and may be tailored to approximate that of an ACL or PCL. Each post 152 may not necessarily extend straight along a longitudinal axis, as shown, and may instead be curved to approximate the curved shape of an ACL or PCL.

Each post 152 includes a convex rounded surface that rotatably and slidably engages with a concave surface of a cam 156 of the recess 157. It is noted that the posts 152 and cams 156 are in sliding contact, but are physically detached from each other. Although not shown, the recess 157 may be formed in a separate insert, like box 11, that is removably attached to the femoral component 158.

Figure 11:
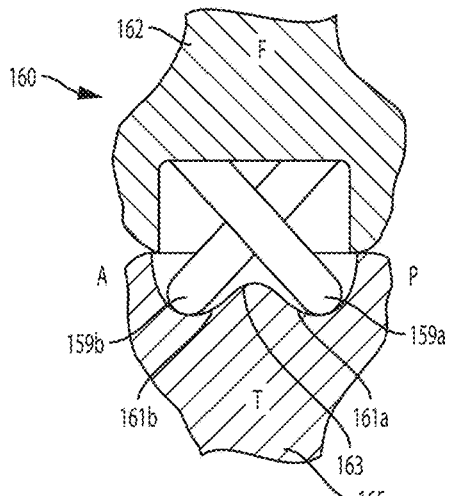
FIG. 11 depicts an alternative embodiment of a knee joint prosthesis, as viewed in a sagittal plane, in which posts, which mimic the ACL and PCL, are disposed on the femoral portion and engage with cams on the tibial portion.

FIG. 11 depicts an alternative embodiment of a knee joint prosthesis 160, which is similar to the knee joint prosthesis 150 with the exception that the posts 159a and 159b are disposed on the femoral component 162 and engage with cams 161a and 161b, respectively, disposed on a recess 163 that is formed on the articular insert 165 of a tibial portion (or the tibial portion itself). The locations of the posts and cams are interchangeable, however, it is noted that the location and geometry of the posts 159a and 159b continue to mimic that of an ACL and PCL, respectively. Also, like the embodiment shown in FIG. 9, and although not shown, each of the articular insert 165 and the femoral component 162 may include one angled post and one cam.

Figure 12:
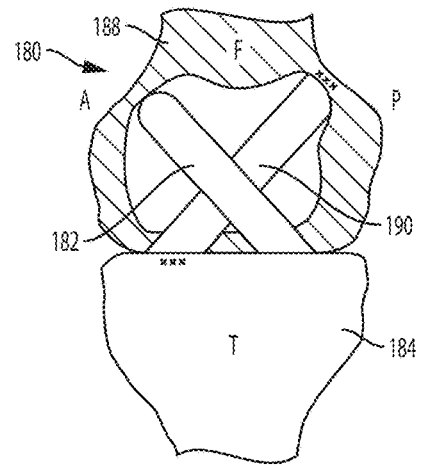
FIG. 12 depicts an alternative embodiment of a knee joint prosthesis, as viewed in a sagittal plane, in which a post, which mimics the PCL, is disposed on the tibial portion and engages with a cam on the femoral portion, and an artificial ligament, which mimics the ACL, is disposed between the tibial portion and the femoral portion.

FIG. 12 depicts an alternative embodiment of a knee joint prosthesis 180. The knee joint prosthesis 180 is similar to the knee joint prosthesis 150, and the primary differences will be described hereinafter. In the knee joint prosthesis 180, a post 182, which mimics the PCL, is disposed on the tibial portion 184 and engages with a cam recess 186 on the femoral portion 188. An artificial ligament 190, which mimics the ACL, is fixed to the tibial portion 184 and the femoral portion 188. Fixation is denoted by the small 'xxx' characters in FIG. 12.

The post 182 extends from the lateral and posterior sides of the articular insert 184 to the medial and anterior sides of the femoral component 188 to mimic the location of the PCL. The ligament 190 extends from the medial and anterior sides of the articular insert 184 to the lateral and posterior sides of the femoral component 188 to mimic the location of the ACL. The ligament 190 is fixedly connected to both the articular insert 184 and the femoral component 188, unlike the post 182. The post 182 and the ligament 190 are oriented cross-wise as viewed in the sagittal and frontal planes, however, the post 182 and the ligament 190 may be oriented cross-wise as viewed in only one of those planes.

Figure 13:
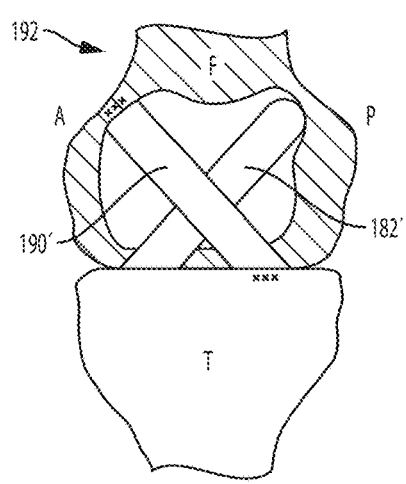
FIG. 13 depicts an alternative embodiment of a knee joint prosthesis, as viewed in a sagittal plane, in which a post, which mimics the ACL, is disposed on the tibial portion and engages with a cam on the femoral portion, and an artificial ligament, which mimics the PCL, is disposed between the tibial portion and the femoral portion.

FIG. 13 depicts an alternative embodiment of a knee joint prosthesis 192 that is similar to the prosthesis 180 with the exception that the locations of the ligament 190' and the post 182' are switched, such that the ligament 190' represents the PCL and the post 182' represents the ACL. As an alternative to FIGS. 12 and 13, the post 182 may be omitted entirely if the natural ACL or PCL of the patient is preserved in a partial knee replacement.

The ligaments shown herein are formed from an artificial material, preferably a synthetic fiber or cord, to replace an ACL or PCL, such that the artificial material is configured similarly to the respective orientation and location of the ACL and PCL in a normal knee. Specifically, the configuration is such that the origin and insertion points of the artificial material in a TKR is similar to the origin and insertion points of the ACL and PCL in a normal knee.

Figure 14:
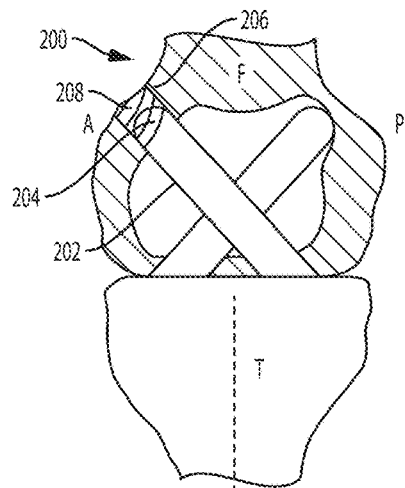
FIG. 14 depicts an alternative embodiment of a knee joint prosthesis, as viewed in a sagittal plane, in which posts, which mimic the ACL and PCL, are disposed on the tibial portion and engage with cams on the femoral portion.

FIG. 14 depicts an alternative embodiment of a knee joint prosthesis 200, which is similar to the knee joint prosthesis 150 with the exception that the free end of the PCL post 202 includes a helical protrusion 204, which may be mechanical threads. The cam 206 in the femoral component, which receives the helical protrusion 204, includes a helical recess 208. The helical recess 208 interacts with the helical protrusion 204 to cause slight rotation about axis Y as the knee joint prosthesis 200 moves between the extended and flexion positions. The slight rotation mimics the slight rotation experienced in a real knee joint when becoming fully extended. The helical surfaces 204 and 208 may, alternatively, be provided in the form of wedged, angled or sloping surfaces.

It should be understood that the term "artificial" means only that it is not the original anatomical ACL or PCL ligament in its original form prior to the TKR, and should not be interpreted as a limitation to the use of only synthetic materials. Accordingly, the artificial ligament, may comprise "natural" materials, such as materials fashioned from biologically created materials and/or may comprise a hybrid of synthetic and natural materials. Other exemplary materials may comprise a variant of a woven polyethylene similar to material previously marketed as SecureStrand® cable, a braided, ultra high molecular weight polyethylene (UHMWPE) cable used for surgical fixation in posterior spinal reconstruction, material currently marketed as Super Cables® (Kinamed, Inc., Camarillo, Calif.) made from UHMWPE and Nylon 6/6,6, Gore-tex® (PTFE fiber manufactured by W.L. Gore and Associates, Inc. Newark, Del.), carbon fiber, or other similar woven materials.

According to various embodiments of the present invention, the artificial material in the form, for example, of artificial ligament may be incorporated into the TKR either at the time of surgery or the TKR may be pre-assembled with the artificial material in advance of surgery. Various methods and devices for connecting the ligament to the tibial and femoral components are described in U.S. Patent App. Pub. No. 2017/0252173 to Garino. As is described in that reference, the locking mechanism for the ends of the artificial ligaments are not limited to any particular construction, and may comprise a spherical retainer, a metal clip, a hook, loops, a fastener in the form of a nail, for example.

In review of the above-described embodiments it should be appreciated that the posts, cams and ligaments can be positioned on or connected to different components and in different locations. Thus, the above-described embodiments should not be viewed as limiting.

Figure 15A:
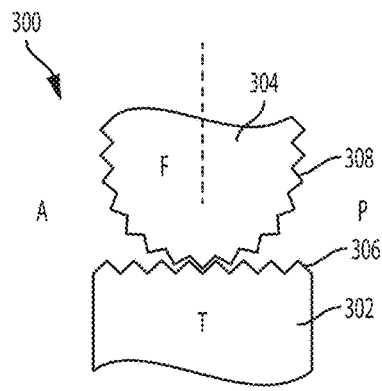
FIGS. 15A and 15B depict side elevation views of an alternative embodiment of a knee joint prosthesis, as viewed in a sagittal plane, in which the tibial portion is coupled to the femoral portion by a geared arrangement. The knee joint prosthesis is shown in an extended position in FIG. 15A and a flexion position in FIG. 15B.
Figure 15B:
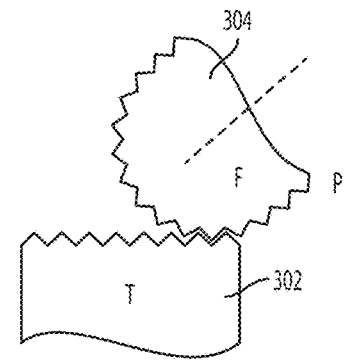

FIGS. 15A and 15B depict side elevation views of an alternative embodiment of a knee joint prosthesis 300, as viewed in a sagittal plane, in which the tibial portion 302 is coupled to the femoral portion 304 by a rack and pinion type geared arrangement. It should be understood that the portion of the knee joint prosthesis 300 shown in FIGS. 15A and 15B does not represent the entire knee joint prosthesis. Rather, the portion of the knee joint prosthesis 300 shown in FIGS. 15A and 15B represents the portions of the tibial portion 302 and femoral portion 304 that contact each other within the area of the box (like box 11). The knee joint prosthesis 300 is shown in an extended position in FIG. 15A and a flexion position in FIG. 15B. The teeth 306 on the tibial portion 302 are meshed with the teeth 308 of the femoral portion 304, such that rotation of the tibial portion 302 causes rotation of the femoral portion 304, and vice versa.

Figure 16A:
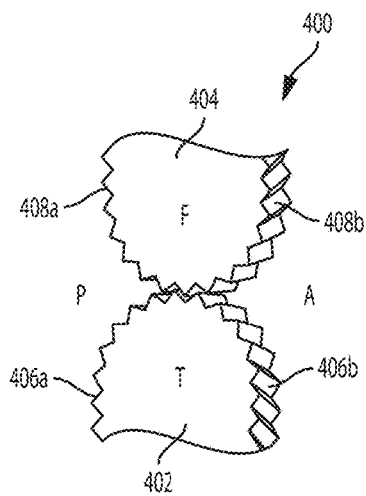
FIG. 16A depicts a side elevation view of an alternative embodiment of a knee joint prosthesis, as viewed in a sagittal plane, in which the tibial portion is coupled to the femoral portion by a geared arrangement, and the geared arrangement is configured to cause medial movement of the tibial portion upon rotation to the extended position. The knee joint is shown from the posterior side in FIG. 16B, and the anterior side in FIG. 16C.
Figure 16B:
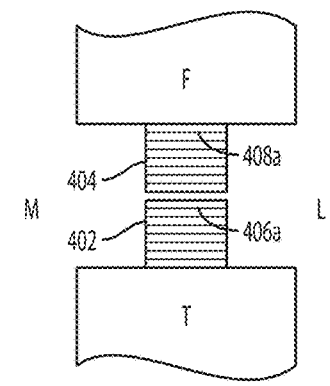
Figure 16C:
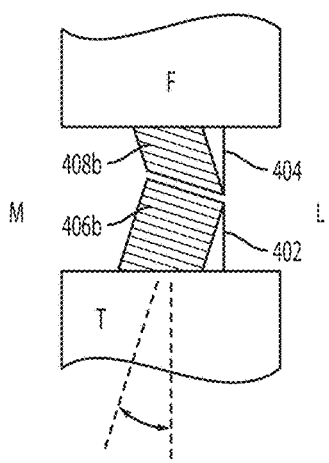

FIGS. 16A-16C depicts an alternative embodiment of a knee joint prosthesis 400, in which the tibial portion 402 is coupled to the femoral portion 404 by a geared arrangement. The knee joint prosthesis 400 is substantially similar to the knee joint prosthesis 300 and the primary differences between those embodiments will be described hereinafter.

The tibial portion 402 includes a rounded and convex outer surface upon which teeth 406 are disposed. The convex outer surface includes a posterior segment 406a having a simple curved path that follows the arc of a circle, and an anterior segment 406b that follows a helical path. The helical path extends medially as viewed in an anterior direction. The teeth also follow the trajectory of the helical path of the anterior portion 406b. The posterior segment 406a intersects the anterior segment 406b in a graduated manner.

Similarly, the femoral portion 404 includes a convex outer surface upon which teeth 408 are disposed. The convex outer surface includes a posterior segment 408a having a simple curved path that follows the arc of a circle, and an anterior segment 408b that follows a helical path. The helical path extends medially as viewed in an anterior direction. It should be understood that the teeth also follow the trajectory of the helical path of the anterior segment 408b. The posterior segment 408a intersects the anterior segment 408b in a graduated manner.

Although both the posterior segment 408a and the anterior segment 408b are shown and described as following a helical trajectory, only one of those segments may follow a helical trajectory.

The teeth 406 on the tibial portion 402 are meshed with the teeth 408 of the femoral portion 404, such that rotation of the tibial portion 402 causes rotation of the femoral portion 404, and vice versa. Also, as the tibial portion 402 rotates in an anterior direction to the extended position, the tibial portion 402 also moves in the medial direction. The slight rotation of the tibial portion 402 in the medial direction mimics the slight rotation experienced in a real knee joint when becoming fully extended. Rotation in the medial direction is due to the helical geometry of the mating anterior portions 406b and 408b. As best shown in those figures, the posterior toothed segment 406a/408a of each of the femoral and tibial gears includes a plurality of interconnected gear teeth, wherein each tooth of the interconnected gear teeth extends (i) along a horizontal longitudinal plane passing through the knee joint prosthesis and (ii) normal to a vertical sagittal plane passing through the knee joint prosthesis. The anterior toothed segment 406b/408b of each of the femoral and tibial gears includes a plurality of interconnected gear teeth, wherein each tooth of the interconnected gear teeth of the anterior toothed segment extends along a plane that is oblique to both the horizontal longitudinal plane and the vertical sagittal plane (see oblique angle arrows shown in FIG. 16C).

Figure 17:
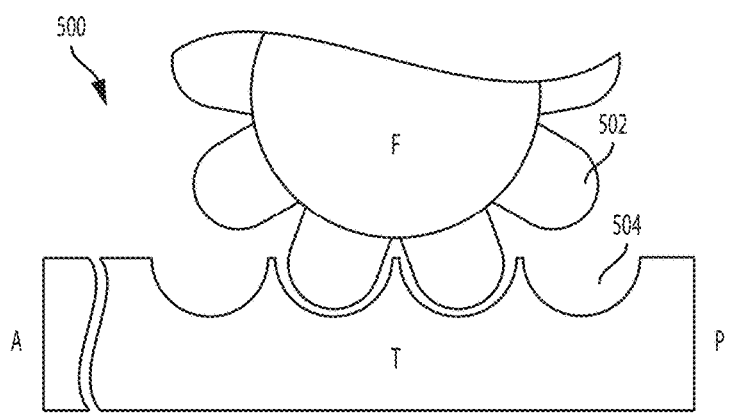
FIG. 17 depicts an alternative embodiment of a knee joint prosthesis, as viewed in a sagittal plane, in which the tibial portion is coupled to the femoral portion by a post and cam arrangement.

FIG. 17 depicts an alternative embodiment of a knee joint prosthesis 500, as viewed in a sagittal plane, in which the tibial portion is coupled to the femoral portion by a post 502 and cam 504 arrangement. The knee joint prosthesis 500 is substantially similar to the knee joint prosthesis 300 with the exception that the teeth 306 and 308 are replaced by posts 502 and cams 504, respectively. It should be understood that the teeth 406 and 408 of the knee joint prosthesis 300 may similarly be replaced by a post and cam arrangement like that of the knee joint prosthesis 500.

Figure 18:
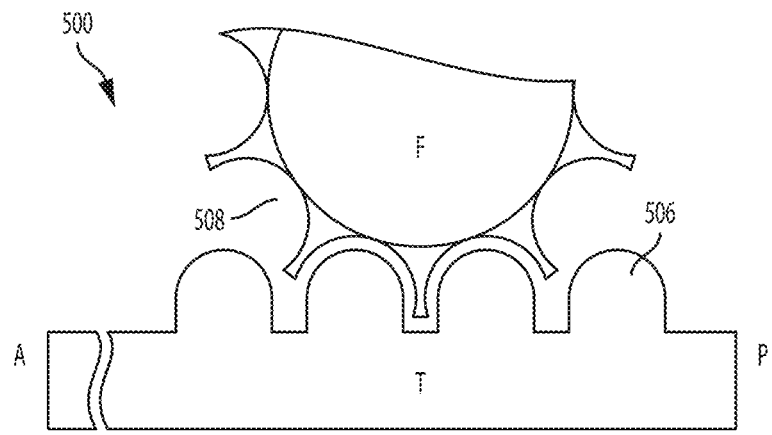
FIG. 18 depicts an alternative embodiment of a knee joint prosthesis, as viewed in a sagittal plane, in which the tibial portion is coupled to the femoral portion by a post and cam arrangement.

As shown in FIG. 18, the placement of the posts 506 and cams 508 can be switched without departing from the scope or spirit of the invention.

Figure 19:
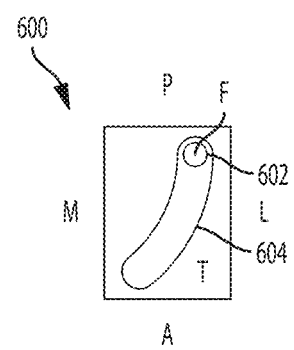
FIG. 19 is a plan view depicting an alternative embodiment of a knee joint prosthesis in which the tibial portion is coupled to the femoral portion by a pin and slot arrangement.

FIG. 19 is a plan view depicting an alternative embodiment of a knee joint prosthesis 600 in which the tibial portion T is coupled to the femoral portion F by a pin 602 and slot 604 arrangement. The knee joint prosthesis 600 is shown in the flexion position in FIG. 19. Like the other embodiments, the portion of the knee joint prosthesis 600 shown in FIG. 19 merely represents the portions of the tibial portion T and the femoral portion F that contact each other within the area of the box (like box 11), as opposed to an entire knee joint prosthesis.

According to this embodiment, the pin 602 is disposed on the femoral portion F and the slot 604 is disposed on the tibial component T, however, the opposite could be true. The pin 602 extends in a vertical direction into the depth of the slot 604. In operation, the pin 602 travels along the length of the slot 604. The slot 604 curves in the medial direction as viewed in an anterior direction.

In operation, as the tibial portion T rotates in an anterior direction to the extended position and the pin 602 travels along the length of the slot 604, the tibial portion T also rotates in the medial direction. The slight rotation of the tibial portion T in the medial direction mimics the slight rotation experienced in a real knee joint when becoming fully extended. Movement in the medial direction is due to the curvature of the slot 604.

The components of the knee joint prosthesis may be made of the same or similar material. In general, however, all materials are preferably inert, not prone to cause infection, and otherwise safe and approved for use as a surgical implant. Exemplary materials include polyethylene, surgically approved metal alloys, surgically approved ceramic materials, or a combination thereof. Any well-known materials in the field of surgical implants may be used to fabricate any of the various embodiments or portions thereof according to the present invention.

While preferred embodiments of the invention have been shown and described herein, it will be understood that such embodiments are provided by way of example only. Numerous variations, changes, and substitutions may occur to those skilled in the art without departing from the spirit of the invention. Accordingly, it is intended that the appended claims cover all such variations that fall within the spirit and scope of the invention.

I claim:

1. A knee joint prosthesis configured to move between an extended position and a flexion position, the knee joint prosthesis comprising:
   a femoral component configured to be mounted to a femur; and
   a tibial component configured to be mounted to a tibia, the tibial component configured to engage the femoral component to form the knee joint prosthesis;
   wherein the femoral component and the tibial component are at least partially connected together by a geared arrangement, the geared arrangement including a femoral gear disposed on the femoral component and a tibial gear disposed on the tibial component, wherein the femoral and tibial gears are meshed together, wherein for each of the femoral and tibial gears, a posterior toothed segment of each gear has a curved path that follows an arc of a circle, and an anterior toothed segment of each gear follows a helical path, wherein the posterior toothed segment of each of the femoral and tibial gears includes a plurality of interconnected gear teeth, wherein each tooth of the interconnected gear teeth extends (i) along a horizontal longitudinal plane passing through the knee joint prosthesis and (ii) normal to a vertical sagittal plane passing through the knee joint prosthesis, and wherein the anterior toothed segment of each of the femoral and tibial gears includes a plurality of interconnected gear teeth, wherein each tooth of the interconnected gear teeth of the anterior toothed segment extends along a plane that is oblique to both the horizontal longitudinal plane and the vertical sagittal plane.

2. The knee joint prosthesis of claim 1, wherein the femoral and tibial gears are meshed together in both the extended and flexion positions.

3. The knee joint prosthesis of claim 1, wherein the femoral and tibial gears are both at least partially cylindrical.

4. The knee joint prosthesis of claim 1, wherein the femoral gear is non-rotatably mounted to the femoral component, and wherein the tibial gear is non-rotatably mounted to the tibial component.

5. The knee joint prosthesis of claim 1, wherein the femoral gear is slanted relative to a planar surface to the femoral component, and wherein the tibial gear is slanted relative to a planar surface to the tibial component.

6. The knee joint prosthesis of claim 1, wherein the femoral and tibial gears are each positioned at a location between adjacent condyles of the knee joint prosthesis.

* * * * *